United States Patent
Grip et al.

(10) Patent No.: US 9,534,994 B1
(45) Date of Patent: Jan. 3, 2017

(54) METHODS, SYSTEMS, AND TEST ARTICLES FOR DETERMINING A FLEXIBILITY VALUE OF A FASTENER

(71) Applicant: The Boeing Company, Chicago, IL (US)

(72) Inventors: Robert Erik Grip, Rancho Palos Verdes, CA (US); Gerald E. Mabson, Bellevue, WA (US)

(*) Notice: Subject to any disclaimer, the term of this patent is extended or adjusted under 35 U.S.C. 154(b) by 822 days.

(21) Appl. No.: 13/958,657

(22) Filed: Aug. 5, 2013

(51) Int. Cl.
*G01N 3/02* (2006.01)
*F16B 21/06* (2006.01)
*G01L 3/14* (2006.01)
*G01N 3/24* (2006.01)

(52) U.S. Cl.
CPC ............ *G01N 3/02* (2013.01); *F16B 21/06* (2013.01); *G01L 3/1464* (2013.01); *G01N 3/24* (2013.01)

(58) Field of Classification Search
USPC .......................................................... 702/33
See application file for complete search history.

(56) References Cited

U.S. PATENT DOCUMENTS

2005/0052000 A1* 3/2005 Barker ................. B60R 21/276
280/728.2

2006/0080069 A1* 4/2006 Fujimoto ............ G06F 17/5018
703/2

OTHER PUBLICATIONS

Gunbring, F. Prediction and Modelling of Fastener Flexibilty Using FE. Linkoping University Department of Management and Engineering [online], 2008 [retrieved on Oct. 15, 2016]. Retrieved from the Internet: <www.diva-portal.org/smash/get/diva2:17841/FULLTEXT01.pdf>.*

* cited by examiner

*Primary Examiner* — Paul D Lee
(74) *Attorney, Agent, or Firm* — Smith Moore Leatherwood LLP (57) ABSTRACT

Methods, systems, and apparatuses for determining a flexibility value K of a fastener. An illustrative system includes a test apparatus including three straps with a strain gauge coupled to each strap. A fastener, such as a bolt, is installed through the straps, with a tensile or compressive force then applied to the test apparatus. Responsively, the strain gauges generate signals indicative of elastic deformation of the straps. The signals are transmitted to a signal processor, which may display deformation values, or alternatively, may process the signals to calculate the value K. The elastic deformation values acquired from the strain gauges, together with cross sectional area and elastic moduli of the straps, are entered into a calculation which applies a predetermined relationship to arrive at the value K. The test apparatus may be a stand-alone device for use in calculating the value K.

37 Claims, 4 Drawing Sheets

METHODS, SYSTEMS, AND TEST ARTICLES FOR DETERMINING A FLEXIBILITY VALUE OF A FASTENER

BACKGROUND

Design of assemblies having fastened joints may require knowledge of fastener flexibilities for various types of fasteners in various materials. For a given joint geometry and fastener type, determining the percentage of load carried by each individual fastener depends, in part, upon the flexibility value of each fastener.

Methodologies for theoretically calculating fastener flexibilities are known. However, the values of fastener flexibility obtained using these methodologies may have questionable accuracy and reliability. For example, calculated results may not agree between the various theoretical methods.

Thus, obtaining fastener flexibilities from test data is desirable. However, known test methods may be associated with various drawbacks, such as the need to use sensitive and expensive test instrumentation as well as uncertainty and/or inaccessibility of the measurement locations of interest.

SUMMARY

Accordingly, methods, systems, and test articles for determining a flexibility value K of a fastener may find utility.

An example implementation of the present disclosure may include a system having a test apparatus including a stack of three straps or strata, with a strain gauge coupled to at least some of the straps. A fastener to be tested, such as a bolt, is installed through the test apparatus, with a tensile or compressive force then applied to the test apparatus. Responsively, the strain gauges generate signals indicative of elastic deformation of the straps. The signals are transmitted to a signal processor, which may display deformation values, or alternatively, which may process the signals to calculate the value K. The elastic deformation values acquired from the strain gauges, together with cross sectional area and elastic moduli of the straps, are entered into a calculation which applies a predetermined relationship to arrive at the value K. The test apparatus may be a stand-alone device for use in calculating the value K.

One example of the disclosure relates to a system for determining a flexibility value K of a fastener. The system includes a test apparatus, or article, including a first strap, or stratum, having a cross-sectional area $A_o$ and an elastic modulus $E_o$, a second stratum having a cross-sectional area $A_o$ and an elastic modulus $E_o$, and a third stratum having a cross-sectional area $A_i$ and an elastic modulus $E_i$. The first, second, and third strata form a stack where the third stratum is between the first stratum and the second stratum. The stack includes a first end portion and a second end portion opposite the first end portion. The stack further includes a virtual axis extending from the first end portion of the stack to the second end portion of the stack. The stack also includes a virtual neutral section perpendicular to the virtual axis. The virtual neutral section has an infinitesimal thickness along which an elastic deformation $\epsilon_1$ of each of the first stratum and the second stratum, and an elastic deformation $\epsilon_2$ of the third stratum, responsive to a tensile or compressive force P imposed on the third stratum in a direction along the virtual axis, are substantially equal. The stack further includes a through opening configured to receive the fastener an interval L from the virtual neutral section along the virtual axis. A first deformation sensor is coupled to the first stratum within the interval L from the virtual neutral section along the virtual axis. Similarly, a second deformation sensor is coupled to the second stratum, also within the interval L from the virtual neutral section along the virtual axis. The system also includes a signal processor electrically coupled to the first deformation sensor and to the second deformation sensor to receive signals therefrom.

In one example, which may include at least a portion of the subject matter of any of the preceding and/or following examples, the system includes a third deformation sensor configured to measure the deformation of the third stratum when the tensile or compressive force P is imposed on the third stratum, wherein the signal processor electrically is coupled to the third deformation sensor to receive signals therefrom.

One example of the present disclosure relates to a method of determining a flexibility value K of a fastener. The method may include selecting a first stratum, a second stratum, and a third stratum, wherein each of the first stratum and the second stratum has a cross-sectional area $A_o$ and an elastic modulus $E_o$, and the third stratum has a cross-sectional area $A_i$ and an elastic modulus $E_i$. The method includes forming a stack from the first, second, and third strata, where the third stratum is between the first stratum and the second stratum. The stack including a first end portion opposite the first end portion, a virtual axis extending from the first end portion to the second end portion, and a virtual neutral section perpendicular to the virtual axis and having an infinitesimal thickness along which an elastic deformation $\epsilon_1$ of each of the first stratum and the second stratum and an elastic deformation $\epsilon_2$ of the third stratum, responsive to a tensile or compressive force P imposed on the third stratum in a direction along the virtual axis, are equal or substantially equal. The method further includes installing the fastener into the through opening in the stack an interval L from the virtual neutral section along the virtual axis, wherein, within the interval L, an elastic deformation $\epsilon_0$ of each of the first stratum and the second stratum is not equal to an elastic deformation $\epsilon_1$ of the third stratum, responsive to the tensile or compressive force P imposed on the third stratum in the direction along the virtual axis. The method also includes imposing the tensile or compressive force P on the third stratum in the direction along the virtual axis, measuring the elastic deformation $\epsilon_0$ of each the first stratum and the second stratum within the interval L, and determining the flexibility value K based upon a predetermined relationship among the elastic modulus $E_o$ and the elastic modulus $E_i$, the cross-sectional area $A_o$ and the cross-sectional area $A_i$, and the elastic deformation $\epsilon_0$.

In one example of the method, which may include at least a portion of the subject matter of any of the preceding and/or following examples, installing the fastener into the through opening in the stack also includes installing the fastener such that it fully penetrates the through opening.

In one example of the method, which may include at least a portion of the subject matter of any of the preceding and/or following examples, the through opening is generally perpendicular to the virtual axis.

In one example, which may include at least a portion of the subject matter of any of the preceding and/or following examples, the method also includes eliminating a preload in the stack in the direction perpendicular to the virtual axis.

In one example of the method, which may include at least a portion of the subject matter of any of the preceding and/or following examples, the predetermined relationship is $$K = \frac{\varepsilon_O(A_O E_O)(A_i E_i)}{L[P - \varepsilon_O(2A_O E_O + A_i E_i)]}.$$

In one example of the method, which may include at least a portion of the subject matter of any of the preceding and/or following examples, measuring the elastic deformation $\epsilon_0$ of each of the first stratum and the second stratum in the direction along the virtual axis also includes measuring strain of each of the first stratum and the second stratum while the tensile or compressive force P is imposed on the third stratum.

In one example of the method, which may include at least a portion of the subject matter of any of the preceding and/or following examples, forming the stack that includes the virtual neutral section includes coupling the first stratum, the second stratum, and the third stratum at the first end portion of the stack.

In one example of the method, which may include at least a portion of the subject matter of any of the preceding and/or following examples, coupling the first, second, and third strata includes bonding the first stratum to the third stratum, and bonding the second stratum to the third stratum, along the virtual axis 240.

In one example of the method, which may include at least a portion of the subject matter of any of the preceding and/or following examples, a first bonded region between the first stratum and the third stratum is at least partially coextensive along the virtual axis with a second bonded region between the second stratum and the third stratum. Ends of the first bonded region and the second bonded region proximal the through opening, are vertically aligned when the virtual axis is horizontal.

In one example of the method, which may include at least a portion of the subject matter of any of the preceding and/or following examples, coupling the first stratum, the second stratum, and the third stratum includes welding the first stratum to the third stratum and welding the second stratum to the third stratum.

In one example of the method, which may include at least a portion of the subject matter of any of the preceding and/or following examples, a first weld joint between the first stratum and the third stratum is at least partially coextensive along the virtual axis with a second weld joint between the second stratum and the third stratum. Ends of the first weld joint and the second weld joint, generally perpendicular to the virtual axis and proximal the through opening, are vertically aligned when the virtual axis is horizontal.

In one example of the method, which may include at least a portion of the subject matter of any of the preceding and/or following examples, installing the fastener into the through opening in the stack comprises installing a first fastener into the first through opening in the stack, and forming the stack that comprises the virtual neutral section includes installing a second fastener along the virtual axis an interval 2L away from the first fastener into a second through opening in the stack.

One example of the present disclosure relates to a test article for use in determining a flexibility value K of a fastener. The test article includes a first stratum having a cross-sectional area $A_o$ and an elastic modulus $E_o$, a second stratum having a cross-sectional area $A_o$ and an elastic modulus $E_o$, and a third stratum having a cross-sectional area $A_i$ and an elastic modulus $E_i$. The first, second, and third strata form a stack where the third stratum is between the first stratum and the second stratum. The stack includes a first end portion and a second end portion opposite the first end portion. The stack further includes a virtual axis extending from the first end portion of the stack to the second end portion of the stack. The stack also includes a virtual neutral section perpendicular to the virtual axis. The virtual neutral section has an infinitesimal thickness along which an elastic deformation $\epsilon_1$ of each of the first stratum and the second stratum and an elastic deformation $\epsilon_2$ of the third stratum (responsive to a tensile or compressive force P imposed on the third stratum in a direction along the virtual axis) are equal or substantially equal.

In one example, which may include at least a portion of the subject matter of any of the preceding and/or following examples, the test article also includes a first deformation sensor coupled to the first stratum within an interval L from the virtual neutral section along the virtual axis, and a second deformation sensor coupled to the first stratum within an interval L from the virtual neutral section along the virtual axis.

In one example of the test article, which may include at least a portion of the subject matter of any of the preceding and/or following examples, the first and second deformation sensors are strain gauges.

In one example of the test article, which may include at least a portion of the subject matter of any of the preceding and/or following examples, the test article also includes a third deformation sensor coupled to the first stratum within the interval L from the virtual neutral section along the virtual axis.

In one example of the test article, which may include at least a portion of the subject matter of any of the preceding and/or following examples, the third deformation sensor is a strain gauge.

In one example of the test article, which may include at least a portion of the subject matter of any of the preceding and/or following examples, the stack includes a through opening substantially perpendicular to the virtual axis and located the interval L from the virtual neutral section along the virtual axis.

In one example of the test article, which may include at least a portion of the subject matter of any of the preceding and/or following examples, the through opening is a pilot opening having a smaller diameter than the fastener.

In one example of the test article, which may include at least a portion of the subject matter of any of the preceding and/or following examples, the through opening is a final opening.

In one example of the test article, which may include at least a portion of the subject matter of any of the preceding and/or following examples, the through opening is a first through opening configured to receive a first fastener. The stack also includes the second through opening, configured to receive a second fastener. The second through opening is displaced along the virtual axis an interval 2L from the first through opening.

In one example of the test article, which may include at least a portion of the subject matter of any of the preceding and/or following examples, the first through opening and the second through opening are pilot openings having smaller diameters than the first fastener and the second fastener.

In one example of the test article, which may include at least a portion of the subject matter of any of the preceding and/or following examples, the first through opening and the second through opening are final openings sized to receive the first fastener and the second fastener.

In one example, which may include at least a portion of the subject matter of any of the preceding and/or following examples, the test article also includes a first coupling between the first stratum and the third stratum, and a second coupling between the second stratum and the third stratum. The first coupling is at least partially coextensive along the virtual axis with the second coupling.

In one example of the test article, which may include at least a portion of the subject matter of any of the preceding and/or following examples, ends of the first coupling and the second coupling, generally perpendicular to the virtual axis and proximal the through opening, are vertically aligned when the virtual axis is horizontal.

In one example of the test article, which may include at least a portion of the subject matter of any of the preceding and/or following examples, the first coupling and the second coupling are bonds.

In one example of the test article, which may include at least a portion of the subject matter of any of the preceding and/or following examples, the bonds are welds.

In one example of the test article, which may include at least a portion of the subject matter of any of the preceding and/or following examples, a cross-sectional area $A_o$ of the first and second strata is greater than a cross-sectional area $A_i$ of the third stratum.

In one example of the test article, which may include at least a portion of the subject matter of any of the preceding and/or following examples, $A_o$ is less than $A_i$.

In one example of the test article, which may include at least a portion of the subject matter of any of the preceding and/or following examples, $A_o$ is equal to $A_i$.

In one example of the test article, which may include at least a portion of the subject matter of any of the preceding and/or following examples, an elastic modulus $E_o$ of the first and second strata is greater than an elastic modulus $E_i$ of the third stratum.

In one example of the test article, which may include at least a portion of the subject matter of any of the preceding and/or following examples, $E_o$ is less than $E_i$.

In one example of the test article, which may include at least a portion of the subject matter of any of the preceding and/or following examples, $E_o$ is equal to $E_i$.

In one example of the test article, which may include at least a portion of the subject matter of any of the preceding and/or following examples, a ratio of a larger one of the elastic modulus $E_o$ and the elastic modulus $E_i$ to a smaller one of the elastic modulus $E_o$ and the elastic modulus $E_i$ is in the range from 1 to 10.

In one example of the test article, which may include at least a portion of the subject matter of any of the preceding and/or following examples, a proportion of a larger one of the elastic modulus $E_o$ and an elastic modulus of the fastener to a smaller one of the elastic modulus $E_o$ and the elastic modulus of the fastener is in the range from 1 to 10.

BRIEF DESCRIPTION OF THE DRAWINGS

Having thus described examples of the disclosure in general terms, reference will now be made to the accompanying drawings, which are not necessarily drawn to scale, and wherein like reference characters designate the same or similar parts throughout the several views, and wherein:

DETAILED DESCRIPTION

Figure 1:
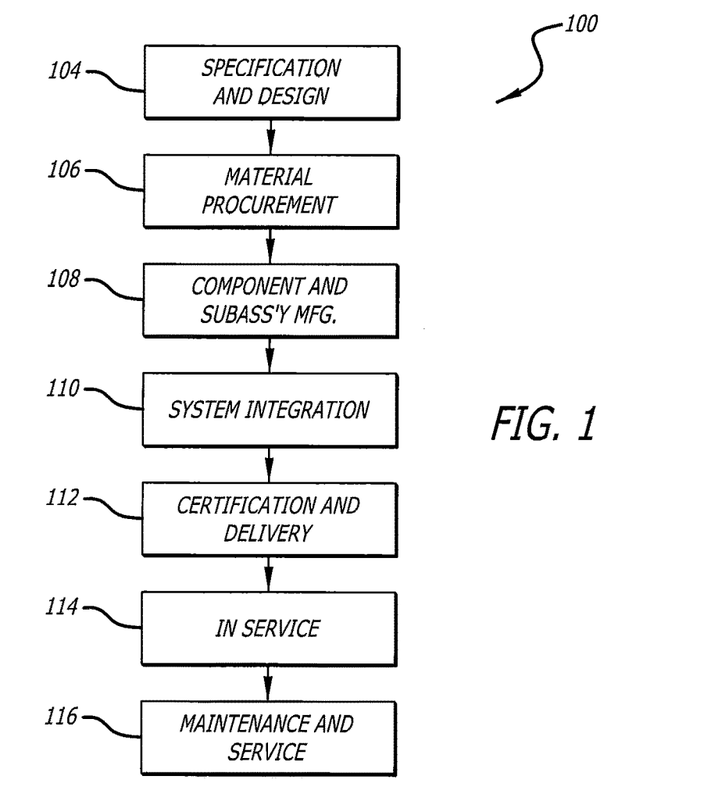
FIG. 1 is a flow diagram of aircraft production and service methodology.
Figure 2:
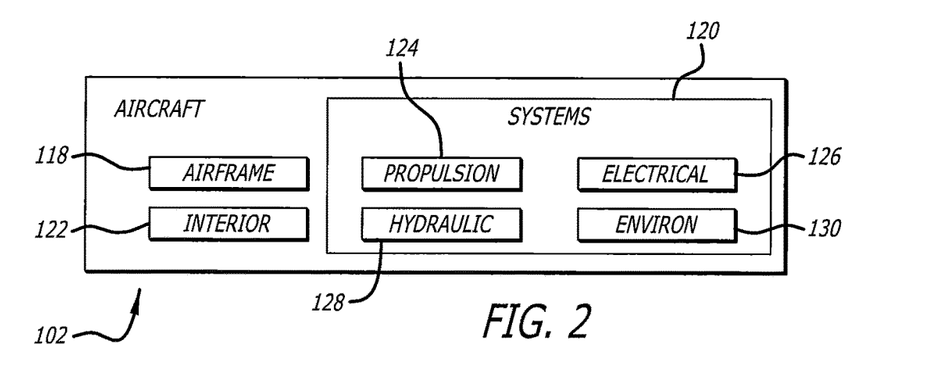
FIG. 2 is a block diagram of an aircraft.

Examples of the disclosure may be described in the context of an aircraft manufacturing and service method 100 as shown in FIG. 1 and an aircraft 102 as shown in FIG. 2. During pre-production, exemplary method 100 may include specification and design 104 of the aircraft 102 and material procurement 106. During production, component and subassembly manufacturing 108 and system integration 110 of the aircraft takes place. Thereafter, the aircraft 102 may go through certification and delivery 112 in order to be placed in service 114. While in service by a customer, the aircraft 102 is scheduled for routine maintenance and service 116 (which may also include modification, reconfiguration, refurbishment, and so on).

Each of the processes of method 100 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 2, the aircraft 102 produced by exemplary method 100 may include an airframe 118 with a plurality of systems 120 and an interior 122. Examples of high-level systems 120 include one or more of a propulsion system 124, an electrical system 126, a hydraulic system 128, and an environmental system 130. Any number of other systems may be included. Although an aerospace example is shown, the principles of the invention may be applied to other industries, such as the automotive industry.

Apparatus and methods shown or described herein may be employed during any one or more of the stages of the production and service method 100. For example, components or subassemblies corresponding to production process 108 may be fabricated or manufactured in a manner similar to components or subassemblies produced while the aircraft 102 is in service. Also, one or more realizations of the apparatus, method, or combination thereof may be utilized during the production states 108 and 110, for example, by substantially expediting assembly of or reducing the cost of an aircraft 102. Similarly, one or more of apparatus or method realizations, or a combination thereof, may be utilized while the aircraft 102 is in service, for example and without limitation, to maintenance and service 116.

Figure 3:
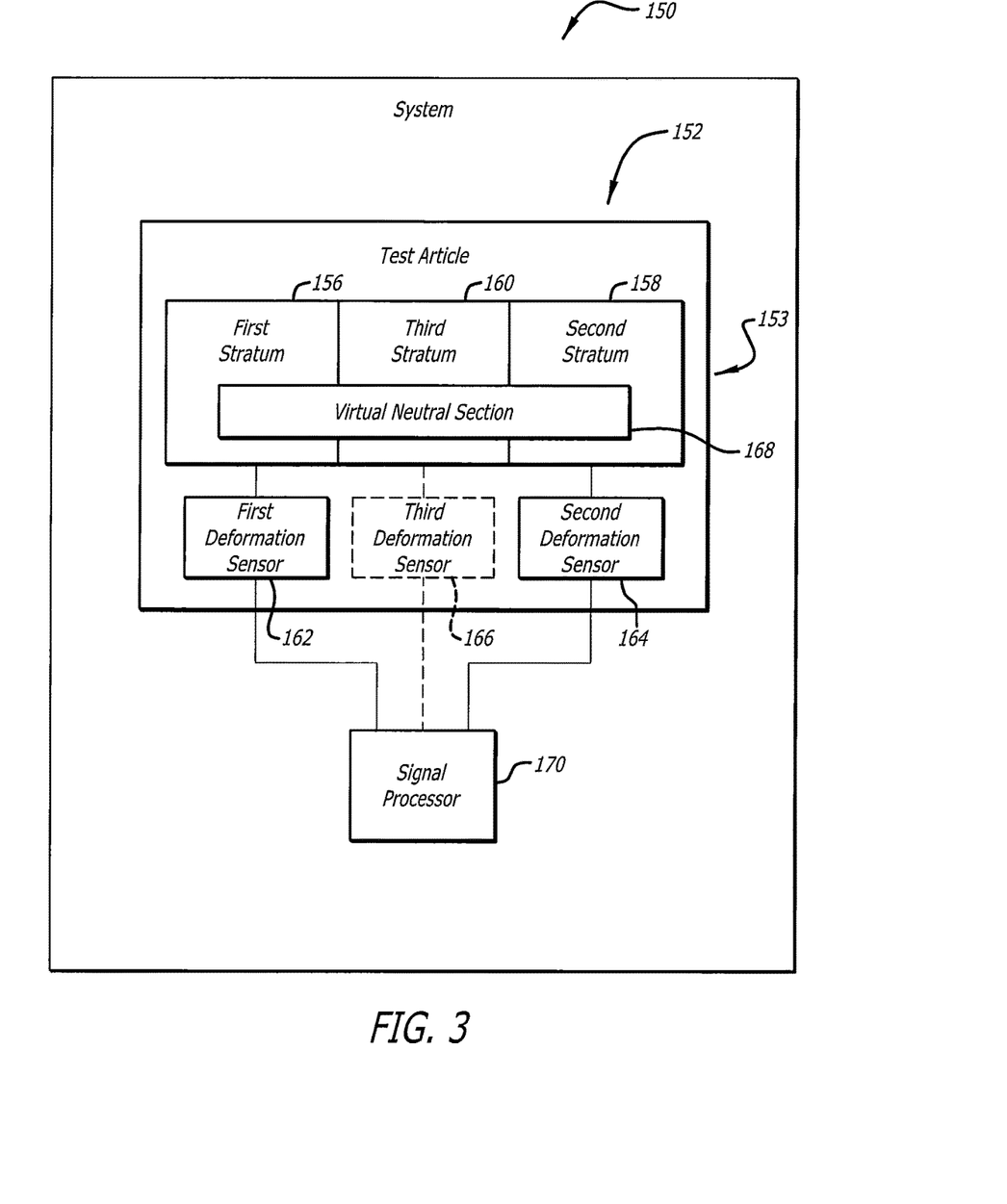
FIG. 3 is a block diagram of a system for determining a flexibility value K of a fastener, according to an aspect of the present disclosure.

As illustrated in FIG. 3, one example of the disclosure relates to a system 150 for determining a flexibility value K of a fastener. The system 150 includes a test article 152 including a first stratum 156, having a cross-sectional area $A_o$ and an elastic modulus $E_o$, a second stratum 158, having a cross-sectional area $A_o$ and an elastic modulus $E_o$, and a third stratum 160, having a cross-sectional area $A_i$ and an elastic modulus $E_i$. The cross-sectional areas $A_o$ and $A_i$ and the elastic moduli $E_o$ and $E_i$ are obtained from empirical measurements. The first, second, and third strata 156, 158, 160 form a stack 153 (FIGS. 4 and 5) where the third stratum 160 is between the first stratum 156 and the second stratum 158. The stack 153 includes a first end portion, e.g., a first end portion 236 illustrated in FIG. 4, and a second end portion, e.g., a second end portion 238 (FIG. 4), opposite the first end portion. The stack 153 has a virtual axis 240 (illustrated, e.g., in FIG. 4), extending from the first end portion 236 of the stack 153 to the second end portion 238. The stack 153 also includes a virtual neutral section 168, perpendicular to the virtual axis 240. The virtual neutral section 168 has an infinitesimal thickness along which an elastic deformation $\epsilon_1$ of each of the first stratum 156 and the second stratum 158, and an elastic deformation $\epsilon_2$ of the third stratum 160, responsive to a tensile or compressive force P imposed on the third stratum 160 in a direction along the virtual axis, are equal or substantially equal. The stack 153 further includes a through opening 230 (see FIG. 4) configured to receive the fastener (e.g., a bolt 10) an interval L from the virtual neutral section 168 along the virtual axis 240. A first deformation sensor 162 is coupled to the first stratum 156 within the interval L from the virtual neutral section 168 along the virtual axis. Similarly, a second deformation sensor 164 is coupled to the second stratum 158, also within the interval L from the virtual neutral section 168 along the virtual axis 240. The system 150 also includes a signal processor 170 electrically coupled to the first deformation sensor 162 and to the second deformation sensor 164 to receive signals therefrom.

Those skilled in the art will appreciate that to accurately calculate fastener flexibility K, the cross sectional area of the strata 156, 158, 160 and the interval L will be selected such that the stiffness of the strata is of the same order of magnitude as that of the bolt.

In FIG. 3, lines connecting various elements and/or components of the system 150 may represent electrical, mechanical, fluid, optical, electromagnetic, and other couplings and/or combinations thereof. Couplings other than those depicted in FIG. 3 may also exist. Dashed lines connecting the various elements and/or components of the system 150 may represent couplings similar in function and purpose to those represented by solid lines; however, couplings represented by the dashed lines relate to alternative or optional aspects of the disclosure. Likewise, elements and/or components of the system 150 represented in dashed lines represent alternative or optional aspects of the disclosure.

In one example, the system 150 includes a third deformation sensor 166 configured to measure the deformation of the third stratum 160 when the tensile or compressive force P is imposed on the third stratum 160, wherein the signal processor 170 is electrically coupled to the third deformation sensor to receive signals therefrom. Measurements acquired by the third deformation sensor 166 may additionally increase accuracy of calculated fastener flexibility values.

In one aspect of the disclosure, strata 156, 158, and 160 may be made of various materials including metals, such as aluminum, steel, or titanium, as well as composites, such as carbon fiber reinforced plastics.

Signals, indicative of measured deformation, generated by the first and second deformation sensors 162, 164, and where provided, by the third deformation sensor 166, are transmitted to the signal processor 170 for subsequent processing. Processing may include storage, display, algorithmic processing, further transmission, other manipulation, or any combination of these. The signal processor 170 may therefore include a memory or other data storage device, a transducer for rendering the electrical signal into another type of signal or into digital form, a display enabling an observer to read measured values acquired from the deformation sensors, a data processor such as a personal computer, communications apparatus, and may include any combination of thereof, or may take other forms.

Figure 4:
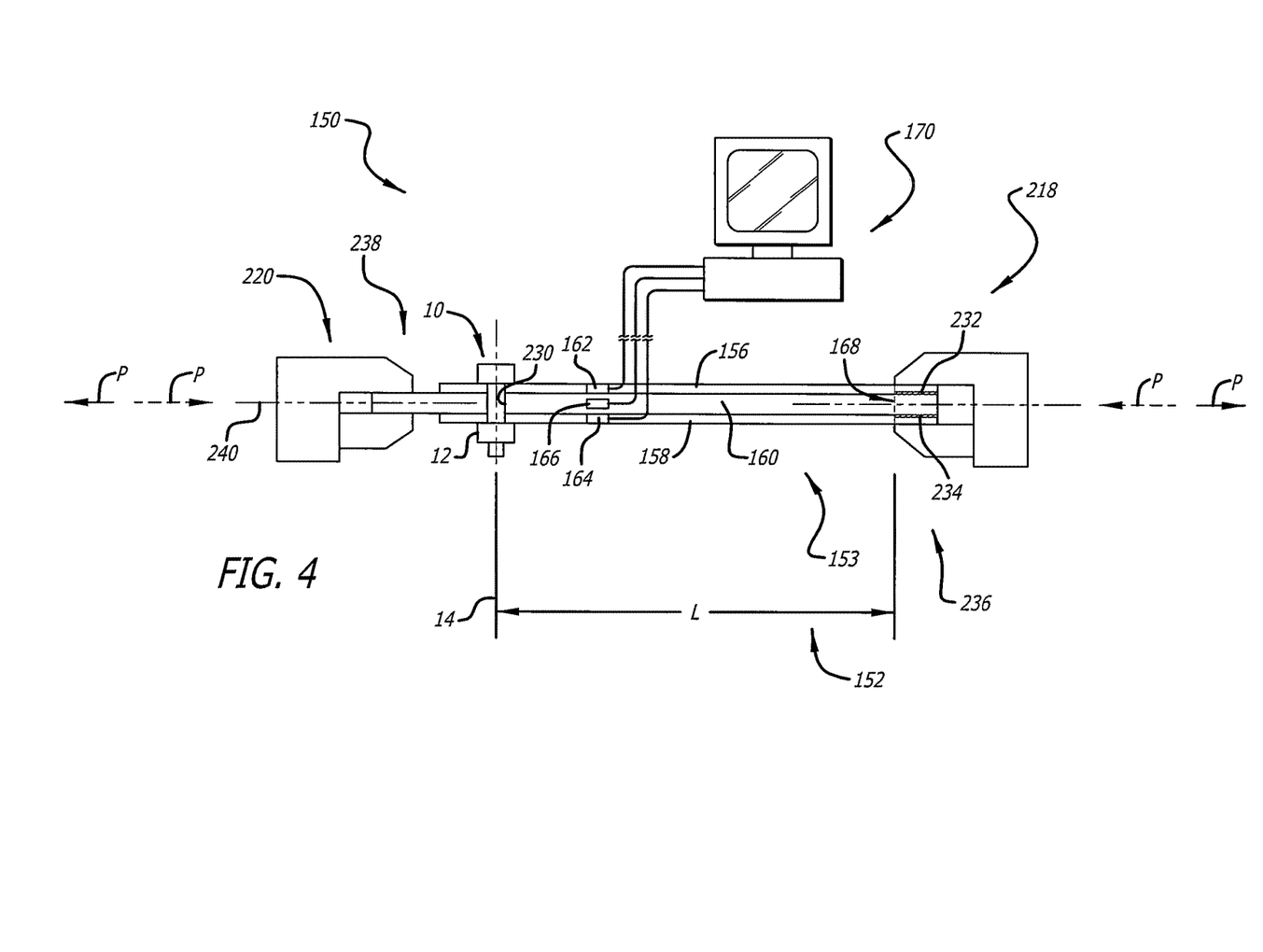
FIG. 4 is an elevational view of the system illustrated in FIG. 3, wherein a single fastener is employed, according to at least one aspect of the present disclosure.

Referring to FIG. 4, another example of the present disclosure relates to the test article 152.

In one example of the test article 152, the first and second deformation sensors 162, 164 are strain gauges. Values measured by the strain gauges will be used to calculate the fastener flexibility value K, as described below.

In one example, the test article 152 also includes the third deformation sensor 166, coupled to the first stratum 156 within the interval L (FIG. 4) from the virtual neutral section 168 (FIG. 4) along the virtual axis 240. Use of the third deformation sensor 166 may promote accuracy of measured deformation values.

In one example of the test article 152, the third deformation sensor 166 is a strain gauge. As mentioned previously, values measured by the strain gauges will be used to calculate the fastener flexibility value K.

In one example of the test article 152, the stack 153 includes the through opening 230 (FIG. 4), substantially perpendicular to the virtual axis 240 and located the interval L from the virtual neutral section 168 along the virtual axis 240. Forming the through opening 230 perpendicular to the axis 240 may promote accuracy of measurement of the values used in the calculation of flexibility value K.

In one example of the test article 152, the through opening 230 is a pilot opening. The pilot opening may be enlarged, as necessary, so that fasteners, such as screws, pins, rivets, etc., of different sizes may be tested to determine fastener flexibility value. Those skilled in the art will appreciate that the pilot opening may be enlarged by drilling or reaming, for example.

In one example of the test article 152, the through opening 230 is a final opening. The final opening has a diameter complementary to that of the fastener to be installed therein. The final opening enables ready installation of the fastener for testing.

Figure 5:
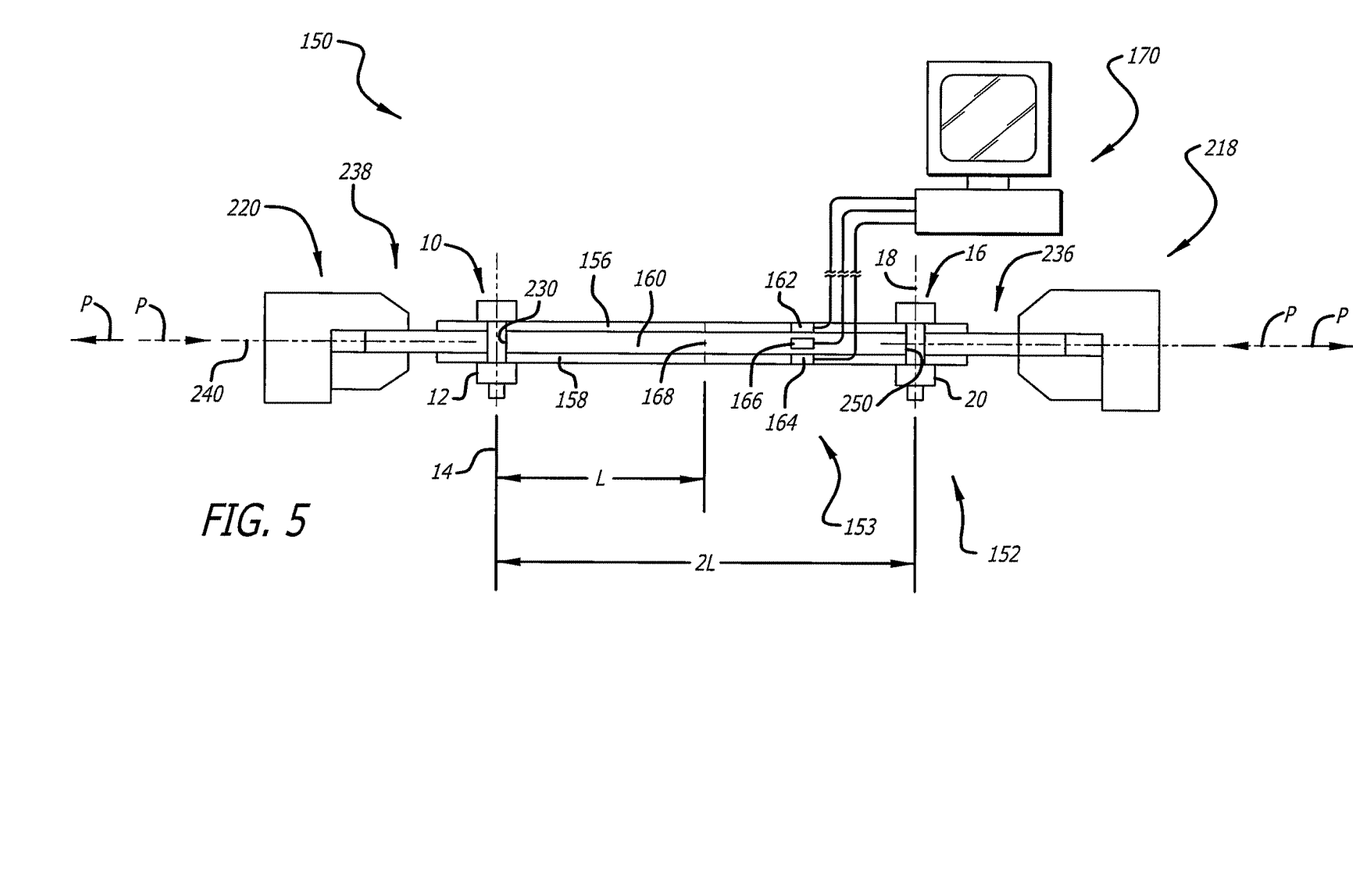
FIG. 5 is an elevational view of the system illustrated in FIG. 3, wherein two fasteners are employed, according to a further aspect of the present disclosure.

As illustrated in FIG. 5, in still another example of the test article 152, the through opening is a first through opening 230 configured to receive a first fastener, such as the fastener 10. The stack 153 further includes a second through opening 250, configured to receive a second fastener, such as the fastener 16. The second through opening 250 is displaced along the virtual axis 240 an interval 2L from the first through opening 230. Provision of two through openings 230, 250 permits installation therein of two fasteners (e.g., the fasteners 10 and 16). The longitudinal axis 14 of the first fastener (e.g., the bolt 10) and the longitudinal axis 18 of the second fastener (e.g., the bolt 16) are separated by the interval 2L. In this example of the test article, the virtual neutral section 168 bisects the interval 2L into two parts, each equal to the interval L in length.

In one example of the test article 152 illustrated in FIG. 5, the first through opening 230 and the second through opening 250 are pilot openings having smaller diameters than their respective fasteners (e.g., the fasteners 10 and 16). As mentioned above, the pilot opening may be enlarged, as necessary, so that fasteners of different sizes may be tested to determine flexibility value K thereof.

In one example of the test article 152, the first through opening 230 and the second through opening 250 are final openings sized to receive their respective fasteners, such as the fasteners 10, 16. The final openings permit installation of two fasteners 10, 16 therein without the need to enlarge the openings.

In one example illustrated in FIG. 4, the test article 152 includes a first coupling 232 between the first stratum 156 and the third stratum 160, and a second coupling 234 between the second stratum 158 and the third stratum 160. The first coupling 232 is at least partially coextensive along the virtual axis 240 with the second coupling 234.

In one example of the test article 152, the first coupling 232 and the second coupling 234 are bonds. A bond may encompass the use of adhesives, chemical fusion, frictionally interfitting members, or the use of joining methods, such as soldering or brazing.

In one example of the test article 152, the bonds are welds. In some applications, welds may be potentially more durable and reliable than other types of bonds.

In one example of the test article 152, $A_o$ of the first and second strata 156, 158 is greater than $A_i$ of the third stratum 160. Selecting the first and second strata 156, 158 to have these characteristics may enable determination of fastener flexibility value using a test article 152 wherein outer strata (such as the first and second strata 156, 158) are thicker than a central stratum (such as the third stratum 160).

In one example of the test article 152, $A_o$ is less than $A_i$. The resultant test article 152 may facilitate effective determination of fastener flexibility value wherein the outer strata (e.g., the first and second strata 156, 158) of the test article 152 are thinner than the central stratum (e.g., the third stratum 160).

In one example of the test article 152, $A_o$ is equal to $A_i$. Selecting the first, second, and third strata 156, 158, 160 to have these characteristics may facilitate determination of fastener flexibility value using a test article 152 wherein the first, second, and third strata 156, 158, 160 are of equal thickness.

In one example of the test article 152, $E_o$ of the first and second strata 156, 158 is greater than $E_i$ of the third stratum 160. The resultant test article 152 may promote effective determination of fastener flexibility value wherein the elastic modulus of the outer strata (i.e., the first and second strata 156, 158) is greater than the elastic modulus of the central stratum (i.e., the third stratum 160).

In one example of the test article 152, $E_o$ is less than $E_i$. The resultant test article 152 may promote effective determination of fastener flexibility value wherein the elastic modulus of the outer strata (i.e., the first and second strata 156, 158) is greater than the elastic modulus of the central stratum (i.e., the third stratum 160).

In one example of the test article 152, $E_o$ is equal to $E_i$. In this example, effective determination of fastener flexibility value using a test article 152 having strata 156, 158, 160 of equal elastic moduli is promoted.

In one example of the test article 152, a ratio of a larger one of the elastic modulus $E_o$ and the elastic modulus $E_i$ to a smaller one of the elastic modulus $E_o$ and the elastic modulus $E_i$ is in the range from 1 to 10. Selecting the first, second, and third strata 156, 158, 160 having these characteristics may improve the accuracy of calculated fastener flexibility values.

In one example of the test article 152, a proportion of a larger one of the elastic modulus $E_o$ and an elastic modulus of the fastener to a smaller one of the elastic modulus $E_o$ and the elastic modulus of the fastener is in the range from 1 to 10. Selecting the first, second, and third strata 156, 158, 160 having these characteristics may improve the accuracy of calculated fastener flexibility values.

A further example of the present disclosure relates to a method of determining a flexibility value K of a fastener. The method may include selecting the first stratum 156, the second stratum 158, and the third stratum 160, wherein each of the first stratum 156 and the second stratum 158 has a cross-sectional area $A_o$ and an elastic modulus $E_o$, and the third stratum 160 has a cross-sectional area $A_i$ and an elastic modulus $E_i$. The method includes forming a stack 153 from the first, second, and third strata 156, 158, 160, wherein the third stratum 160 is between the first stratum 156 and the second stratum 158. The stack 153 includes the first end portion 236 (FIG. 4) and the second end portion 238 opposite the first end portion 236. The stack 153 also includes the virtual axis 240 extending from the first end portion 236 to the second end portion 238, and the virtual neutral section 168 extending perpendicularly to the virtual axis 240.

The virtual axis 240 has the infinitesimal thickness along which an elastic deformation $\epsilon_1$ of each of the first stratum 156 and the second stratum 158 and an elastic deformation $\epsilon_2$ of the third stratum 160 (responsive to the tensile or compressive force P imposed on the third stratum 160 in the direction along the virtual axis) are equal or substantially equal.

The tensile or compressive force P may be generated by a tensile strength tester or a similar machine (neither shown) having gripping jaws and a source of power for translating the jaws apart (to generate tensile forces) or together (to generate compressive forces), for example.

The method may further include installing the fastener (e.g., the fastener 10 in FIG. 4) into the through opening 230 in the stack 153 the interval L from the virtual neutral section 168 along the virtual axis 240, wherein, within the interval L, an elastic deformation $\epsilon_0$ of each of the first stratum 156 and the second stratum 158 is not equal to an elastic deformation $\varsigma_1$ of the third stratum 160, responsive to the tensile or compressive force P imposed on the third stratum 160 in the direction along the virtual axis 240. The method may include: imposing the tensile or compressive force P on the third stratum 160 in the direction along the virtual axis 240; measuring the elastic deformation $\epsilon_0$ of each of the first stratum 156 and the second stratum 158 within the interval L; and determining the fastener flexibility value K based upon a predetermined relationship among the elastic modulus $E_o$, the elastic modulus $E_i$, the cross-sectional area $A_o$, the cross-sectional area $A_i$, and the elastic deformation $\epsilon_0$.

In one example of the method, installing the fastener (e.g., the fastener 10 of FIG. 4) into the through opening 230 (FIG. 4) in the stack 153 also includes installing the fastener such that it fully penetrates the through opening 230.

In one example of the method, the through opening 230 is generally perpendicular to the virtual axis 240. Forming the through opening 230 perpendicular to the virtual axis may promote improved measurement accuracy of the values used to calculate the fastener flexibility value K.

In one example, the method also includes eliminating a preload in the stack 153 in the direction perpendicular to the virtual axis 240. Eliminating preload may also promote accuracy of measurements.

In one example of the method, the predetermined relationship is $$K = \frac{\varepsilon_O(A_O E_O)(A_i E_i)}{L[P - \varepsilon_O(2A_O E_O + A_i E_i)]}.$$

The method including the previously-recited formula utilizes the deformation data acquired from the system 150 to calculate the flexibility value K.

In one example, the method also includes measuring the elastic deformation $\epsilon_0$ of each of the first stratum 156 and the second stratum 158 in the direction along the virtual axis 240. The method further includes measuring strain of each of the first stratum 156 and the second stratum 158 while the tensile or compressive force P is imposed on the third stratum 160. The measured values may be used to calculate fastener flexibility value K by utilizing the previously-recited formula.

In one example of the method, forming the stack 153 that includes a virtual neutral section, such as the virtual neutral section 168, includes coupling the first stratum 156, the second stratum 158, and the third stratum 160 at the first end portion 236 of the stack 153.

In one example of the method, coupling the first, second, and third strata 156, 158 160 includes bonding the first stratum 156 to the third stratum 160, and the second stratum 158 to the third stratum 160 along the virtual axis 240.

In one example of the method, a first bonded region between the first stratum 156 and the third stratum 160 is at least partially coextensive along the virtual axis 240 with a second bonded region between the second stratum 158 and the third stratum 160. Ends of the first bonded region and the second bonded region proximal the through opening 230, are vertically aligned when the virtual axis 240 is horizontal.

In one example of the method, coupling the first stratum 156, the second stratum 158, and the third stratum 160 includes welding the first stratum 156 to the third stratum 160 and the second stratum 158 to the third stratum 160.

In one example of the method, a first weld joint between the first stratum 156 and the third stratum 160 is at least partially coextensive along the virtual axis 240 with a second weld joint between the second stratum 158 and the third stratum 160. Ends of the first weld joint and the second weld joint, generally perpendicular to the virtual axis 240 and proximal the through opening 230, are vertically aligned when the virtual axis 240 is horizontal.

In one example of the method, as illustrated in FIG. 5, wherein installing the fastener into the through opening in the stack 153 comprises installing a first fastener (e.g., the fastener 10) into the first through opening 230 in the stack 153, and forming the stack 153 that comprises the virtual neutral section 168. The method may also include installing a second fastener (e.g., the fastener 16) along the virtual axis an interval 2L away from the first fastener into the second through opening 250 in the stack 153.

By way of non-limiting examples, as shown in FIG. 4, one example method of measuring fastener flexibility may include first measuring the cross-sectional areas and elastic moduli of the strata 156,158,160. The fastener 10 to be tested is then inserted in through opening 230, and the stratum 156,158,160 are welded or otherwise bonded together (to the right of fastener 10 as shown in FIG. 4) to prevent relative longitudinal movement between the stratum. An axial load (tension or compression) is applied to the fastener 10 via one or both of grips 218, 220, and while such axial load is applied and gradually increased, strains are measured on each of the three stratum 156,158,160, using deformation sensors 162, 164, 166. From the data obtained from the deformation sensors, the fastener flexibility of fastener 10 is calculated, using a formula such as disclosed herein. FIG. 5 illustrates one example method of simultaneously measuring the fastener flexibility of two fasteners 10, 16. Such example method may be performed similarly as discussed above with respect to FIG. 4, with the exception that the stratum 156, 158, 160 do not need to be welded or otherwise bonded together, since the extra fastener 16 serves to essentially fix the three stratum 156, 158,160 against relative movement with respect to one another during application of the axial load.

As realized herein, a variety of different aspects, examples, and alternatives of systems, test articles, and methods are disclosed herein that include a variety of components, features, and functionality. It should be understood that the various aspects, examples, and alternatives of systems, test articles and methods disclosed herein are capable of including any of the components, features, and functionality of any of the other aspects, examples, and alternatives of systems, test articles, and methods disclosed herein in any combination, and all of such possibilities are intended to be within the spirit and scope of the present disclosure.

Many modifications and other examples of the disclosure set forth herein will come to mind to one skilled in the art to which the disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Moreover, although the foregoing descriptions and the associated drawings describe example embodiments in the context of certain illustrative combinations of elements and/or functions, it should be appreciated that different combinations of elements and/or functions may be provided by alternative implementations without departing from the scope of the appended claims.

What is claimed is:

1. A method of determining a flexibility value K of a fastener, the method comprising:

selecting a first stratum, a second stratum, and a third stratum, wherein each of the first stratum and the second stratum has a cross-sectional area $A_o$ and an elastic modulus $E_o$, and the third stratum has a cross-sectional area $A_i$ and an elastic modulus $E_i$;

forming a stack that comprises:
  a first end portion and a second end portion opposite the first end portion,
  the first stratum, the second stratum, and the third stratum, each extending from the first end portion of the stack to the second end portion of the stack, wherein the third stratum is between the first stratum and the second stratum,
  a virtual axis extending from the first end portion to the second end portion, and
  a virtual neutral section perpendicular to the virtual axis along which an elastic deformation $\epsilon_1$ of each of the first stratum and the second stratum and an elastic deformation $\epsilon_2$ of the third stratum, responsive to a tensile or compressive force P imposed on the third stratum in a direction along the virtual axis, are equal;

installing the fastener into a through opening in the stack an interval L from the virtual neutral section along the virtual axis, wherein, within the interval L, an elastic deformation $\epsilon_0$ of each of the first stratum and the second stratum is not equal to an elastic deformation $\epsilon_1$ of the third stratum, responsive to the tensile or compressive force P imposed on the third stratum in the direction along the virtual axis;

imposing the tensile or compressive force P on the third stratum in the direction along the virtual axis;

measuring the elastic deformation $\epsilon_0$ of each the first stratum and the second stratum within the interval L; and determining the flexibility value K based upon a predetermined relationship among the elastic modulus $E_o$ and the elastic modulus $E_i$, the cross-sectional area $A_o$ and the cross-sectional area $A_i$, and the elastic deformation $\epsilon_0$.

2. The method of claim 1, wherein the predetermined relationship is $$K = \frac{\varepsilon_O(A_O E_O)(A_i E_i)}{L[P - \varepsilon_O(2A_O E_O + A_i E_i)]}.$$

3. The method of claim 1, wherein measuring the elastic deformation $\epsilon_0$ of each of the first stratum and the second stratum in the direction along the virtual axis comprises measuring strain of each of the first stratum and the second stratum while the tensile or compressive force P is imposed on the third stratum.

4. The method of claim 1, wherein forming the stack that comprises the virtual neutral section includes coupling the first stratum, the second stratum, and the third stratum at the first end portion of the stack.

5. The method of claim 4, wherein coupling the first stratum, the second stratum, and the third stratum comprises bonding the first stratum to the third stratum and bonding the second stratum to the third stratum along the virtual axis.

6. The method of claim 5, wherein a first bonded region between the first stratum and the third stratum is at least partially coextensive along the virtual axis with a second bonded region between the second stratum and the third stratum and wherein ends of the first bonded region and the second bonded region, generally perpendicular to the virtual axis and proximal the through opening, are vertically aligned when the virtual axis is horizontal.

7. The method of claim 4, wherein coupling the first stratum, the second stratum, and the third stratum comprises welding the first stratum to the third stratum and the second stratum to the third stratum.

8. The method of claim 7, wherein a first weld joint between the first stratum and the third stratum is at least partially coextensive along the virtual axis with a second weld joint between the second stratum and the third stratum and wherein ends of the first weld joint and the second weld joint proximal the through opening are vertically aligned when the virtual axis is horizontal.

9. The method of claim 1, wherein installing the fastener into the through opening in the stack comprises installing a first fastener into a first through opening in the stack, and forming the stack that comprises the virtual neutral section includes installing a second fastener along the virtual axis an interval 2L away from the first fastener into a second through opening in the stack.

10. The method of claim 1, wherein installing the fastener into the through opening in the stack further includes installing the fastener such that the fastener fully penetrates the through opening.

11. The method of claim 1, wherein the through opening is generally perpendicular to the virtual axis.

12. The method of claim 1, further comprising eliminating a preload in the stack in the direction perpendicular to the virtual axis.

13. A test article for use in determining a flexibility value K of a fastener, the test article comprising:

a first stratum having a cross-sectional area $A_o$ and an elastic modulus $E_o$;

a second stratum having a cross-sectional area $A_o$ and an elastic modulus $E_o$; and a third stratum having a cross-sectional area $A_i$ and an elastic modulus $E_i$, wherein the first stratum, the second stratum, and the third stratum form a stack with the third stratum between the first stratum and the second stratum, the stack comprising:

a first end portion and a second end portion opposite the first end portion, wherein each of the first stratum, the second stratum, and the third stratum extends from the first end portion of the stack to the second end portion of the stack;

a virtual axis extending from the first end portion to the second end portion; and a virtual neutral section perpendicular to the virtual axis along which an elastic deformation $\epsilon_1$ of each of the first stratum and the second stratum and an elastic deformation $\epsilon_2$ of the third stratum, responsive to a tensile or compressive force P imposed on the third stratum in a direction along the virtual axis, are equal.

14. The test article of claim 13, further comprising a first deformation sensor coupled to the first stratum within an interval L from the virtual neutral section along the virtual axis, and a second deformation sensor coupled to the first stratum within an interval L from the virtual neutral section along the virtual axis.

15. The test article of claim 14, wherein the first deformation sensor and the second deformation sensor each comprise a strain gauge.

16. The test article of claim 13, further comprising a third deformation sensor coupled to the third stratum within an interval L from the virtual neutral section along the virtual axis.

17. The test article of claim 16, wherein the third deformation sensor comprises a strain gauge.

18. The test article of claim 13, wherein the stack comprises a through opening substantially perpendicular to the virtual axis and located an interval L from the virtual neutral section along the virtual axis.

19. The test article of claim 18, wherein the through opening is a first through opening configured to receive a first fastener, and the stack further comprises a second through opening configured to receive a second fastener and displaced along the virtual axis an interval 2L from the first through opening.

20. The test article of claim 19, wherein the first through opening and the second through opening are pilot openings having smaller diameters than the first fastener and the second fastener.

21. The test article of claim 19, wherein the first through opening and the second through opening are final openings sized to receive the first fastener and the second fastener.

22. The test article of claim 18, further comprising a first coupling between the first stratum and the third stratum and a second coupling between the second stratum and the third stratum, wherein the first coupling is at least partially coextensive along the virtual axis with the second coupling.

23. The test article of claim 22, wherein ends of the first coupling and the second coupling, generally perpendicular to the virtual axis and proximal the through opening, are vertically aligned when the virtual axis is horizontal.

24. The test article of claim 22, wherein the first coupling and the second coupling are bonds.

25. The test article of claim 24, wherein the bonds are welds.

26. The test article of claim 18, wherein the through opening is a pilot opening having a smaller diameter than the fastener.

27. The test article of claim 18, wherein the through opening is a final opening sized to receive the fastener.

28. The test article of claim 13, wherein $A_o$ is greater than $A_i$.

29. The test article of claim 13, wherein $A_o$ is less than $A_1$.

30. The test article of claim 13, wherein $A_o$ is equal to $A_i$.

31. The test article of claim 13, wherein $E_o$ is greater than $E_i$.

32. The test article of claim 13, wherein $E_o$ is less than $E_i$.

33. The test article of claim 13, wherein $E_o$ is equal to $E_i$.

34. The test article of claim 13, wherein a ratio of a larger one of the elastic modulus $E_o$ and the elastic modulus $E_i$ to a smaller one of the elastic modulus $E_o$ and the elastic modulus $E_i$ is from 1 to 10.

35. The test article of claim 13, wherein a proportion of a larger one of the elastic modulus $E_o$ and an elastic modulus of the fastener to a smaller one of the elastic modulus $E_o$ and the elastic modulus of the fastener is from 1 to 10.

36. A system for determining a flexibility value K of a fastener, the system comprising:
a test article comprising:
a first stratum having a cross-sectional area $A_o$ and an elastic modulus $E_o$;
a second stratum having a cross-sectional area $A_o$ and an elastic modulus $E_o$;
a third stratum having a cross-sectional area $A_i$ and an elastic modulus $E_i$, wherein the first stratum, the second stratum, and the third stratum form a stack with the third stratum between the first stratum and the second stratum, the stack comprising:
a first end portion and a second end portion opposite the first end portion, wherein each of the first stratum, the second stratum, and the third stratum extends from the first end portion of the stack to the second end portion of the stack;
a virtual axis extending from the first end portion to the second end portion;
a virtual neutral section perpendicular to the virtual axis along which an elastic deformation $\epsilon_1$ of each of the first stratum and the second stratum and an elastic deformation $\epsilon_2$ of the third stratum, responsive to a tensile or compressive force P imposed on the third stratum in a direction along the virtual axis, are equal; and
a through opening configured to receive the fastener an interval L from the virtual neutral section along the virtual axis;
a first deformation sensor coupled to the first stratum within the interval L from the virtual neutral section along the virtual axis; and
a second deformation sensor coupled to the second stratum within the interval L from the virtual neutral section along the virtual axis; and
a signal processor electrically coupled to the first deformation sensor and the second deformation sensor to receive signals therefrom.

37. The system of claim 36, further comprising a third deformation sensor configured to measure the deformation of the third stratum when the tensile or compressive force P is imposed on the third stratum, wherein the signal processor is electrically coupled to the third deformation sensor to receive signals therefrom.

* * * * *